Figure 1:
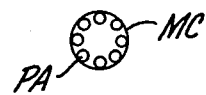
Figure 2:
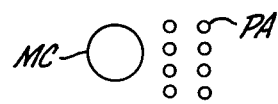
Figure 3:
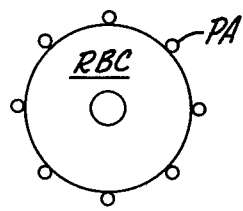
Figure 5:
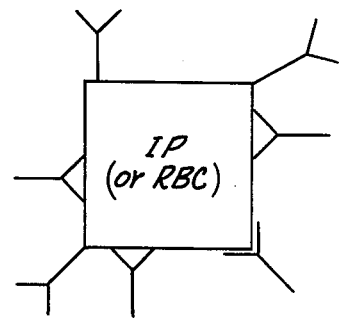
Figure 4A:
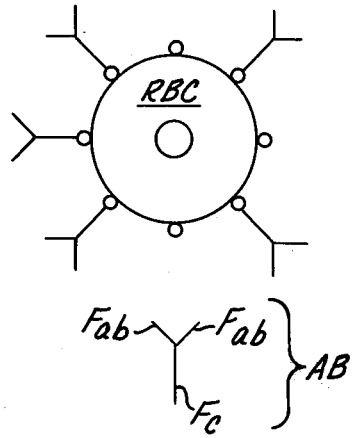
Figure 4B:
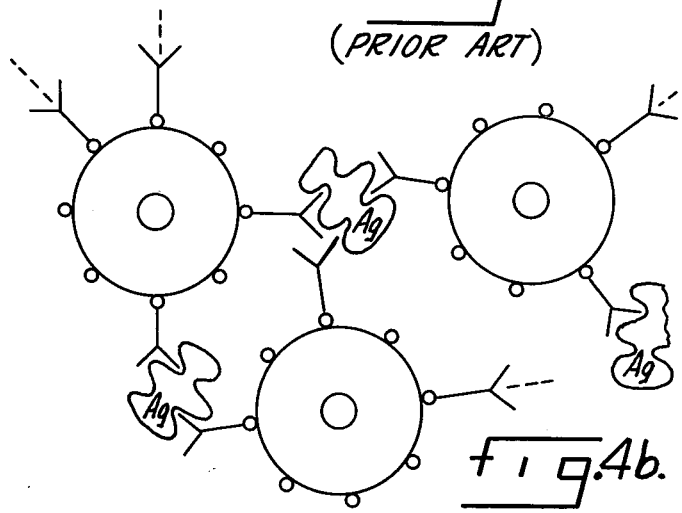
Figure 6A:
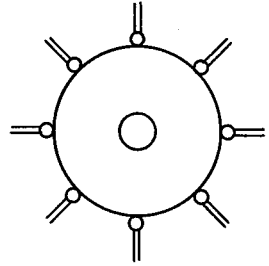
Figure 6B:
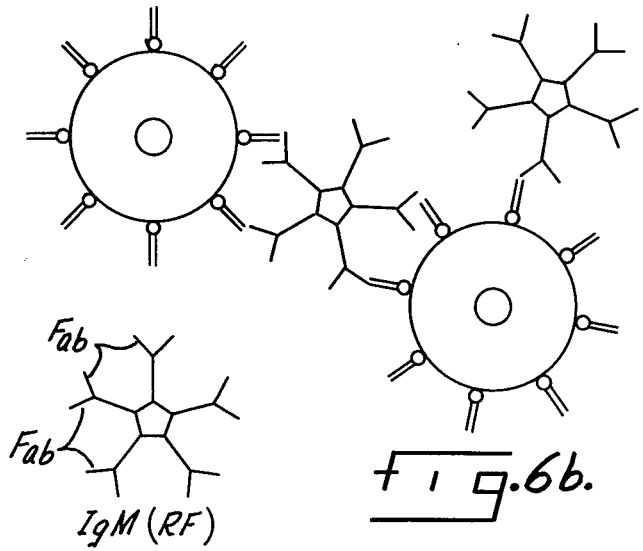

United States Patent [19]

Ainis et al.

[11] 4,189,466
[45] Feb. 19, 1980

[54] DETECTION OF RHEUMATOID FACTOR BY ANTIBODY SENSITIZED MICROBIAL PARTICLES

[75] Inventors: Herman Ainis; Charles F. Lange, both of Evanston; Abraham S. Mark; George H. Scherr, both of Park Forest, all of Ill.

[73] Assignee: Technical Research Affiliates, Inc., Evanston, Ill.

[21] Appl. No.: 875,519

[22] Filed: Feb. 6, 1978

Related U.S. Application Data

[63] Continuation of Ser. No. 614,854, Sep. 19, 1975, abandoned.

[51] Int. Cl.$^2$ ............... G01N 33/16; G01N 31/02
[52] U.S. Cl. ............................... 424/12; 23/230 B; 23/915; 435/7
[58] Field of Search ............... 23/230 B; 424/12; 195/103.5 A, 103.5 R

[56] References Cited

U.S. PATENT DOCUMENTS

| | | | |
|---|---|---|---|
| 3,658,982 | 4/1972 | Reiss | 424/12 |
| 3,689,632 | 9/1972 | Mizushima | 424/12 |
| 3,781,414 | 12/1973 | Huber | 424/12 |
| 3,850,798 | 11/1974 | Sjoquist | 210/31 C |
| 3,873,684 | 3/1975 | Fujita | 424/12 |
| 3,966,898 | 6/1976 | Sjoquist | 424/12 |
| 3,995,018 | 11/1976 | Sjoquist | 424/12 X |

FOREIGN PATENT DOCUMENTS 2322562 5/1974 Fed. Rep. of Germany .
1406964 9/1975 United Kingdom .

OTHER PUBLICATIONS

A. Forsgren et al., J. Immun., 97, 822-827 (1966).
G. Kronvall et al., J. Immun., 103, 828-833 (1969).
Chemical Abstracts, 82:123211v (1975).
Chemical Abstracts, 82:29594a (1975).

*Primary Examiner*—Sidney Marantz
*Attorney, Agent, or Firm*—Kinzer, Plyer, Dorn & McEachran

[57] ABSTRACT

Detection of antigens in a biological specimen of animal origin by means of antibody-sensitized microbial particles, which particles may be sensitized from a whole immunoglobulin fraction, an immunoglobulin fraction derived therefrom (IgG), a purified antibody fraction or the whole serum containing immunoglobulin molecules.

6 Claims, 8 Drawing Figures

DETECTION OF RHEUMATOID FACTOR BY ANTIBODY SENSITIZED MICROBIAL PARTICLES

This is a continuation of application Ser. No. 614,854, filed Sept. 19, 1975, abandoned.

Field of Invention

This invention relates to a method for the detection and quantitation of biologically significant macromolecules and in particular to a method utilizing bacteria as specific antibody binding particles for such detection and quantitation.

Background

The principal attributes of all immunologic reactions are specificity and sensitivity. The specificity of the immunologic reaction is such that, given a complex mixture of molecules, one can detect the presence of a specific molecule or class of molecules in such a mixture. Moreover, utilizing the sensitivity of the immunologic reation, and depending upon the particular technique employed, such detection can be made of exceedingly small quantities of macromolecules. For example, it is possible to distinguish between isomers of a compound (Landsteiner, K. and J. v.d. Scheer, J. Exp. Med., 50; 407,1929) or for that matter, the specificity of the immunological method even permits distinguishing between ortho-or meta-substituted derivatives on a benzene ring, (Boyd, W. C., Fundamentals of Immunology, Interscience Publ., Inc., N.Y., 1947, p. 102) as well as between di- and tri-substituted benzene derivatives. (Boyd, W. C., op. cit; p 105). At the macro-molecular level, it is possible to distinguish between proteins of different animal species as is done in laboratory and clinical immunology (Boyd, W. C.; op. cit. p. 120).

Although the majority of macromolecules are assayed by variations of the precipitin reaction (Mancini, G., et al., 1965, Immunochemistry, 2:235) variations of the agglutination reaction may also be used. For example, inert carrier particles such as bentonite (Bozicevich, J., Tobie, J. E., Thomas, E. H., Hoyem, H. M. & Ward, S. B. A rapid flocculation test for the diagnosis of Trichinosis. Publ. Hlth. Rep. (Wash.) 66:806-814), polystyrene (Singer, J. M. and Plotz, C. M., Am. J. Med., 1956, 21:888, 893) and diverse animal red blood cells (Middlebrook, G. and Dubos, R., J. Exper. Med., 1948, 88:521; Nater, E., Bact. Rev., 1956, 20:166; Boyden, S. V., J. Exper. Med., 1951, 93:107; Stavitsky, A. B., J. Immunol., 1954, 72:360, 368) have been employed in agglutination reactions. All such reactions are passive agglutinations in that the particle which agglutinates is simply a carrier of the immunologically reactive agents that have been placed there by either adsorption (Stavitsky, A. B., J. Immunology, 1954, op. cit.; Singer, J. M. and Plotz, C. M., Amer. J. Med., op. cit.) or chemical coupling (Goodfriend, T. L. et al., 1964, Science, 144:1344) and is not of itself directly involved in the immunologic reaction.

Preciptin reactions such as those performed in gel media usually require many hours of incubation before the end result can be obtained, are restricted to complete antigens, and do not have the desired sensitivity when employed for many diagnostic procedures. Radioimmunoassay circumvents, in part, the time factor, achieves an improved sensitivity, but has a number of undesirable technologic factors such as the hazards of working with radioactive materials and the added expense of instrumentation.

The binding of immunoglobulin G from several animal species, including humans, by means of the Fc portion of the molecule to Protein A-containing strains of Staphylococcus aureus has been demonstrated (Sjoquist et al., Cold Spring Harbor Symp. quant. Biol., 32:577, 1967; Forsgren, A. and Sjoquist, J., J. Immunol., 97:822, 1966; Kronvall, G. and Williams, R. C., Jr., J. Immunology, 103:828, 1969; and Kronvall, G. and Frommel, D., Immunochemistry, 7:124, 1970). This binding is not to be considered as mere adsorption or absorption since principally immunoglobulin G has been shown to effect such binding and apparently only through Fc of the immunoglobulin G molecule.

It was demonstrated, for example, that if the IgG was an antibody directed towards the polysaccharide of a specific type of pneumococcus, a specific mixed agglutination would result between the antibody sensitized staphylococcal cells and the pneumococcus (Kronvall, G. and Williams, R. C., Jr.; op. cit.)

Similarly, the IgG binding capacity of the protein-A containing staphylococcus has been utilized to serve as a solid phase absorbent to separate antibody bound antigen from free antigen in a radio-immunoassay for alpha fetoprotein (Jonsson, S. and Kronvall, G., J. Immunolog., 1:414-415, 1972) and in addition a radioimmunoassay for hepatitis B antigen and antibody (Figenschan, K. J. and Ulstrup, J. C., Acta. path. microbiol. Scand. Section B, 82:422-428, 1974).

The presence in the serum of humans of a rheumatoid factor (RF) has been well documented. (Natvig, J. B., et al., Rheumatoid Arthritis (Ed. by W. Miller) p. 343, Academic Press, London, 1971; Natvig, J. B. and Turner, M. W., 1970, Nature (Lond.) 225:855). The RF has been identified as an antibody response; in most instances of the IgM class, although in some cases that of the IgG class, albeit in all instances with reactivity towards the Fc portion of the IgG molecule.

It occurred to us that a capability of such protein A-containing microbial cells because of their ability to preferentially bind IgG, and also because such binding is oriented through the Fc portion of the Ig G molecule thus leaving the Fab portion free for antibody activity, could serve as a very useful agglutination test system to identify and quantitate many antigens. For example, the mere adsorption of gamma globulins to latex particles in the preparation of a rheumatoid factor test as is currently practiced does in no way insure that only IgG molecules are adsorbed onto the surface, thus reducing significantly the capability of achieving a high degree of sensitivity and specificity. In addition it occurred to us that the utilization of Protein A-containing microbial particles sensitized with isolated Fc fragments of Ig G would serve preferentially for a specific RF-detecting assay. Also, the preferential binding to the Fc portion of IgG by Protein A containing microbial particles insures against the non-specific adsorption and/or binding of molecules that occurs with latex and other hitherto utilized agglutination-detecting systems.

It also occurred to us that the binding of the Ig G antibody to protein A-containing particles would have a stronger bond and therefore result in a more stable preparation than could occur with latex or bentonite particles or similar particles hitherto utilized in the profession where the adsorption to the surface is a weak one and unless highly exacting conditions of pH and ionic concentration of buffer are utilized, would result in separation of the biological product sensitized to such particles.

In addition, the labor, time, and work necessary to effect such agglutinable preparations for diagnostic tests would be reduced since the protein A containing microbial particles would preferentially bind the Ig G and therefore the serum as is recovered from an animal or human containing antibody could be thus used for sensitization without the necessity of a laborious and expensive laboratory procedure to remove the immunoglobulins from the serum in order to concentrate them on latex and other particles hitherto utilized.

The objects therefore, of the present invention are:

To provide a quick, inexpensive, highly specific method for the detection and quantitation of biologically significant molecules.

A second object is to provide a quick, inexpensive and specific (by virtue of Fc-sensitized particles) method for the detection and quantitation of RF in test materials of biological origin.

A third object of the present invention is to provide a Protein A-containing bacterial-antibody sensitized agglutination method which is less time consuming than, but as reliable and sensitive as, those currently employed for detection and quantitation of biologic macromolecules.

One advantage of the present invention is that detection and quantitation of biologically significant macromolecules can be easily carried out therewith by relatively unskilled personnel.

Another advantage of the present invention is that by the use of cell wall fragments of the Protein A containing bacteria, consequent possible complications of whole cell autolytic or exogenous degradation and loss of activity is obviated.

Other objects and advantages of the present invention will be apparent to those skilled in the art from the following description.

Summary of the Invention

In accordance with the present invention there has been developed a method for accurately detecting and quantitating biologic macromolecules which have significance in the diagnosis of disease. This invention permits the detection and quantitation of biologically significant molecules by the use of protein A containing staphylococci which bind via the Fc portion of the specific antibody (immunoglobulin G) molecule which is directed towards the macromolecule to be detected, in a direct passive agglutination reaction. It has also been determined that detection of a macromolecule whose identification and quantitation is desired is significantly enhanced by sensitizing the staphylococci with purified antibody obtained from immunoabsorbent columns. In such procedures the endpoint for the quantitation of a macromolecule whose identification and quantitation is desired is obtained by effecting a series of serial dilutions of the test material mixed with an equal volume of the sensitized staphylococci. That last dilution which gives a visual agglutination multiplied by a "detection factor" of the sensitized particles (the minimum amount the particle is capable of detecting) will give a quantitative value to the test sample.

The invention is also designed to detect and semiquantitate the presence of the rheumatoid factor (RF). In this procedure the Protein A containing microbial cells are sensitized with an Fc fragment of human IgG. Semiquantitation is obtained by serial dilutions of the material to be tested which is mixed with an equal volume of the Fc sensitized microbial cells. The endpoint or titer is the highest dilution of the test serum which gives a visible agglutination of the particles.

In summary, the present invention relates to Protein A containing microbial cells-immunoglobulin combinates wherein they are employed in a novel, sensitive, immunologic assay which can detect and quantitate antigens for which an antibody exists, whether of human or animal origin, as well as for detection and quantitation of rheumatoid factor.

The term antigen as used above is meant to include any biological macromolecule, whether natural or synthesized, which reacts with specific antibody.

The term Protein A-containing microbial cell as used herein is meant to include any Protein A containing microbial cell whether used as the intact cell, cell wall fragment, cell membrane, or any soluble substance or derivative thereof.

The term Protein A containing microbial cell-immunoglobulin combinate as used above is meant to include any whole immunoglobulin molecule, immunoglobulin fraction derived therefrom, or whole serum containing immunoglobulin molecules.

The Detailed Description of the Invention

The following examples are given by way of illustration only:

Example 1.

A culture of protein A containing *S. aureus*, strain G128 was inoculated into 250 ml of Todd Hewitt Broth contained in 1-liter Erlenmeyers and shaken on a reciprocating shaker for 9 hours at 35° C. incubation.

The culture thus recovered was spun at 3000 rpm for 45 minutes at 5° C. temperature, resuspended in saline and adjusted to a #9 MacFarland nephelometer reading. The saline suspended cells were then heat-treated in a water bath maintained at 80° C. for 15 minutes with constant stirring and immediately cooled thereafter.

The culture suspension of *S aureus* thus prepared is washed approximately 5-7 times by centrifugation and resuspended using phosphate buffer at pH 7.3 (PBS).

Suspend 10 mg of the washed cell suspension as prepared above in 5 ml of phosphate buffered saline, pH 7.4 (PBS) and add to this suspension 0.2 ml of an Fc fragment preparation of human IgG immunoglobulin prepared in accord with method as described by Adelman et al. (J. Exptl. Med., 112:203, 1960).

After 10 minutes of stirring at room temperature, the mixture is centrifuged at 5000 rpm, in the cold, and the pellet washed 3 times with PBS and finally resuspended in 5 ml of PBS. The preparation may be used as is or may be treated with a few drops of a dilute dye such as Safranin which serves to color-code the preparation and also acts as a visual aid in detecting the end result of the agglutination reaction.

In order to demonstrate that the Fc fraction was, in fact, coupled to the protein A-containing micrococci utilized in this example and thereby have acquired the capability to detect Rheumatoid Factor when present in sera, and also to demonstrate an enhanced specificity of such an Fc sensitized protein A carrying cell preparation for Rheumatoid Factor, the following series of samples of sera were analyzed by five methods. The "Behring" analysis was performed using the Rheumatoid Factor test kit "Rapi/tex" (Behring Diagnostics, Somerville, N. J.).

The column designated as "Hyland" was performed in accord with the directions of a Rheumatoid Factor detecting kit, "RA-TEST" (Hyland Div. Travenol Laboratories, Costa Mesa, Calif.)

The Fc determinations represent the material prepared as described above and the Waaler-Rose titers represent rheumatoid factor agglutinins in which the numerator where shown was determined by a human gamma globulin-latex-sensitized antigen and the denominator was determined by a rabbit gamma-globulin-sensitized antigen. Diagnosis of the patient, where known, is as indicated.

It is quite clear from this series that we have achieved a preparation using an Fc coupled protein A-containing particle which readily functions as a detector of Rheumatoid Factor. It also can be seen that, in innumerable cases, especially those where no clear diagnostic picture for Rheumatoid arthritis exists, that the degree of agglutination is oftentimes absent or decreased with the Fc-prepared material than with the Hyland or even with the Behring test reagents.

| COMPARATIVE RESULTS FOR RHEUMATOID FACTOR AGGLUTINATION TESTS | | | | | |
|---|---|---|---|---|---|
| Sample Code No. | Behring | Teehnam Fc | Hyland | Waaler-Rose Titer | Diagnosis |
| 82-80 E | − | − | − | | |
| 82-80 F | +++ | +++ | +++ | | |
| 82-80 G | − | − | − | | |
| 82-80 H | ++++ | ++++ | ++++ | 640/160 | arthritis |
| 82-80 I | ++++ | + | ++++ | | |
| 82-80 J | − | − | − | | hyper gamma |
| 82-80 K | ++++ | ++++ | ++++ | 1280/160 | arthritis |
| 82-80 L | ++++ | ++ | ++++ | 640/320 | |
| 82-80 M | − | − | − | | |
| 82-80 N | − | − | − | | |
| 82-80 O | ++++ | ++++ | ++++ | 640/1280 | |
| 82-80 P | − | − | − | 160/320 | arthritis |
| 82-80 Q | − | − | ++ | | prostate carcinoma |
| 82-80 R | − | − | − | | |
| 82-80 S | − | − | − | | |
| 82-80 T | − | − | − | | carcinoma penis |
| 82-80 U | ++ | +/− | ++ | | |
| 82-80 V | − | − | + | | hyper gamma, cirrhosis |
| 82-80 W | − | − | *** | | hyper gamma, pleural affusion |
| 82-80 X | +/− | − | +++ | | hyper gamma, cirrhosis |
| 82-80 Y | − | − | ++ | | hyper gamma, alcoholic |
| 82-80 Z | ++++ | ++++ | ++++ | 2560/640 | tina synamitis |
| 82-80 AA | − | + | + | | hyper gamma |
| 82-80 AB | +/− | − | − | | hyper gamma, anemia hepatomy |
| 82-80 AC | + | − | ++ | | hyper gamma, cirrhosis |
| 82-80 AD | − | − | − | | hyper gamma, alsin |
| 82-80 AE | +++ | + | ++++ | | hypergamma, jaundice |
| 82-80 AF | − | ++++ | + | | hyper gamma |
| 82-81 A | ++ | + | ++ | | hyper gamma, cirrhosis |
| 82-81 B | − | − | − | | gastro-intestinal bleeding |
| 82-81 C | − | − | − | | VDRL R-2 |
| 82-81 D | − | − | + | | VDRL R-2 |
| 82-81 E | − | − | − | | VDRL R-2 |
| 82-81 F | − | − | − | | VDRL WR |
| 82-81 G | − | − | − | | VDRL R-2 |
| 82-81 H | − | − | − | | VDRL R-2 |
| 82-81 I | − | − | − | | VDRL WR |
| 82-81 J | − | − | − | | VDRL WR |
| 82-81 K | − | − | − | | VDRL WR |
| 82-81 L | − | − | − | | VDRL WR |
| 82-81 M | − | − | − | | VDRL WR |
| 82-81 N | − | + | ++ | | — |
| 82-81 O | − | − | + | | carcinoma prostate |
| 82-81 P | − | − | ++ | | carcinoma prostate |
| 82-81 Q | − | − | − | | VDRL WR |
| 82-81 R | − | − | − | | VDRL R-1 |
| 82-81 S | − | − | +++ | | VDRL R-2 |
| 82-81 T | − | − | − | | VDRL WR |
| 82-81 U | − | − | − | | VDRL WR |
| 82-81 V | − | − | + | | Cirrhosis |
| 82-81 W | − | − | − | | VDRL WR |
| 82-81 X | − | − | − | | VDRL R-2 |
| 82-81 Y | − | − | − | | VDRL R-2 |
| 82-81 Z | − | − | − | | |
| 82-81 AA | − | − | − | | Obstructive jaundice |
| 82-81 AB | − | − | − | | VDRL WR |
| 82-81 AC | − | − | − | | Carcinoma Prostate |
| 82-81 AD | − | − | − | | VDRL R-2 |
| 82-81 AE | + | + | ++ | | VDRL R-1 |
| 82-81 AF | − | − | − | | VDRL R-1 |
| 82-81 AG | − | − | ++ | | VDRL R-4 |
| 82-82 V | − | − | − | | R/O collagen dis. |
| 82-82 W | − | − | − | | |
| 82-82 X | − | − | − | | hyper gamma |

-continued
COMPARATIVE RESULTS FOR RHEUMATOID FACTOR AGGLUTINATION TESTS

| Sample Code No. | Behring | Teehnam Fc | Hyland | Waaler-Rose Titer | Diagnosis |
|---|---|---|---|---|---|
| 82-82 Y | − | − | − | | BPH |
| 82-82 Z | ++++ | ++++ | ++++ | 2560/2560 | arthritis |
| 82-82 AA | − | − | − | | hyper gamma monocytopenia |
| 82-82 AB | − | − | − | | hyper gamma |
| 82-82 AC | − | − | − | | VDRL WR |
| 82-82 AD | − | − | − | | VDRL WR |
| 82-82 AE | − | − | − | | VDRL R-2 |
| 82-82 AF | − | − | − | | VDRL R-1 |
| 82-82 A | +++ | + | +++ | −/60 | |
| 82-82 B | − | − | − | | |
| 82-82 C | ++++ | ++++ | ++++ | −/160 | R. A. |
| 82-82 D | ++++ | ++++ | ++++ | −/160 | R. A. |
| 82-82 E | ++++ | ++++ | ++++ | | R. A. |
| 82-82 F | ++++ | ++++ | ++++ | | R. A. |
| 82-82 G | ++++ | ++++ | ++++ | −/640 | R. A. |
| 82-82 H | ++++ | ++++ | ++++ | −/320 | R. A. |
| 82-82 J | − | − | − | | |
| 82-82 K | − | − | − | | |
| 82-82 L | ++++ | ++++ | ++++ | −/512 | R. A. |
| 82-82 M | ++++ | ++++ | ++++ | −/160 | R. A. |
| 82-82 N | − | − | − | | |
| 82-82 P | + | + | +++ | | |
| 82-82 Q | +++ | +++ | +++ | | R. A. |
| 82-82 R | ++++ | ++++ | ++++ | −/160 | R. A. |
| 82-82 S | ++++ | ++++ | ++++ | −/320 | R. A. |
| 82-82 T | +++ | +++ | +++ | −/80 | R. A. |
| 82-82 U | ++++ | ++++ | ++++ | | R. A. |
| 82-83 B | − | − | − | | |
| 82-83 C | ++ | ++ | +++ | | |
| 82-83 D | − | − | +/− | | |
| 82-83 E | − | − | + | | |
| 82-83 F | ++++ | ++++ | ++++ | 1280/neg. | |
| 82-83 G | ++++ | ++++ | ++++ | | |
| 82-83 H | − | − | − | | |
| 82-83 I | − | − | + | | hyper gamma |
| 82-83 J | − | + | ++ | | |
| 82-83 K | − | − | − | | |
| 82-83 L | − | − | + | | hyper gamma, hepatitis |
| 82-83 M | − | − | − | | hyper gamma |
| 82-83 N | − | − | + | | |
| 82-83 O | − | − | − | | VDRL R-2 |
| 82-83 P | − | − | − | | hydrothorax RF (- |
| 82-83 Q | − | − | − | | carcinoma penis |
| 82-83 R | − | − | − | | |
| 82-83 S | − | − | − | | carcinoma prostate |
| 82-83 T | + | ++ | +++ | | hyper gamma, liver failure |
| 82-83 U | + | + | ++ | | hyper gamma, alcoh. liver |
| 82-83 V | − | − | ++ | | hyper gamma, AVH |
| 82-83 W | ++ | − | + | | hyper gamma |
| 82-83 X | − | − | − | | hyper gamma, cirrhosis |
| 82-83 Y | − | + | ++ | | hyper gamma, cirrhosis |
| 82-83 Z | − | − | − | | VDRL + |
| 82-83 AA | − | − | − | | carcinoma penis |
| 82-83 AB | − | − | − | | carcinoma prostate |
| 82-83 AC | − | − | +/− | | |
| 82-83 AD | | | | | |
| 71-43 T | ++ | ++ | +++ | 320/320 | cirrhosis |
| 71-43 R | +++ | ++ | ++++ | 2560/2560 | rheum. arthritis |
| 71-43 F | +++ | +++ | ++++ | 1280/2560 | AVH |
| 71-43 E | ++++ | +++ | ++++ | 160/320 | Alc. Liver dis. |
| 71-43 D | ++ | ++ | +++ | 160/neg. | rheum. arthritis |
| 71-43 S | ++++ | ++++ | ++++ | | |
| 71-43 H | + | + | ++ | 80/neg. | CRF |
| 71-43 G | − | − | − | | |
| 71-43 U | − | − | − | 80/neg. | CVA |
| 82-94 K | ++ | + | +++ | 640/neg. | Arthritis |
| 82-94 L | − | − | | | |
| 82-94 N | − | + | ++ | | |
| 82-94 O | +++ | ++ | +++ | 640/40 | |
| 82-94 P | − | + | ++ | 640/320 | Cellulitis |
| | − | + | + | | |
| | +/− | + | ++ | | |
| | − | − | | | |
| 82-94 T | ++++ | ++++ | ++++ | 320/neg. | |
| 82-94 U | +++ | +++ | +++ | 320/640 | cirrhosis |
| 82-94 V | +++ | ++ | +++ | 640/640 | |
| 71-43 X | + | + | ++ | 1600/40 | AVH |
| 82-94 X | ++ | + | ++ | | Arthritis (neg.) |

-continued

COMPARATIVE RESULTS FOR RHEUMATOID FACTOR AGGLUTINATION TESTS

| Sample Code No. | Behring | Teehnam Fc | Hyland | Waaler-Rose Titer | Diagnosis |
|---|---|---|---|---|---|
| 71-43 Y | ++ | + | +++ | 320/320 | Cirrhosis |
| 82-94 Z | ++ | ++ | ++ | | |
| 71-43 M | − | + | + | | |
| 82-94 AB | − | − | − | | hyper gamma, acute hematurea |
| 71-44 A | − | + | ++ | 160/neg. | bronchial asthma |
| 82-94 AD | − | + | ++ | | |
| 82-94 A | ++++ | ++++ | ++++ | | |
| 82-94 AF | − | − | − | | |
| 71-43 Q | ++ | + | ++ | 160/320 | |
| 71-44 C | + | + | ++ | 320/80 | |
| 82-94 AI | +++ | +++ | +++ | | anemia |
| 71-43 P | + | + | ++ | 160/20 | alcoholism |
| 71-44 B | + | + | + | 320/320 | cirrhosis |
| 82-95 D | +++ | ++ | +++ | 1280/160 | arthritis |
| 71-43 N | ++ | ++ | ++ | 80/neg. | R/O, dermatomyasitis |
| 82-95 F | +++ | +++ | ++++ | 640/1280 | |
| 82-95 G | − | − | +/− | | |
| 82-95 H | − | − | − | | |
| 71-44 P | ++++ | ++++ | ++++ | 640/640 | chronic hepatitis |
| 71-44 N | ++++ | ++++ | ++++ | 1280/640 | heptomegaly |
| 71-44 M | − | + | ++ | 160/neg | R/O SLE |
| 71-44 K | + | + | ++ | 640/320 | AVH |
| 71-44 Q | + | + | ++ | 640/640 | |
| 82-95 A | − | − | − | | |
| 82-95 N | +/− | − | + | | |
| 82-95 O | − | − | − | | hypergamma abscess |
| 82-95 P | − | − | − | | |
| 82-95 Q | − | − | − | | carcinoma prostate |
| 82-95 R | − | + | + | 160/20 | |
| 82-95 S | − | − | + | 160/320 | arthritis |
| 71-44 L | ++ | ++ | +++ | 320/neg. | alcoh. liver |
| 71-44 J | + | + | ++ | 160/160 | pancreatitis |
| 71-44 H | + | + | ++ | 320/320 | |
| 71-44 G | ++ | + | ++ | 320/80 | cirrhosis |
| 71-44 F | ++ | + | +++ | 2560/1280 | rheumatoid arthritis |
| 71-44 D | − | + | ++ | 160/160 | alcoholism |
| 71-44 E | + | + | ++ | 640/160 | gout |
| 82-95 AA | − | − | − | | carcinoma prostate |
| 82-95 AB | − | + | ++ | | hyper gamma |
| 82-95 AC | − | − | +/− | | hyper gamma |
| 82-95 AD | − | − | − | | carcinoma prostate |
| 82-95 AE | − | − | − | | hyper gamma, alcoholic |
| 82-95 AF | − | + | ++ | | hyper gamma, liver dis. |

In looking at sera which clearly were negative in any degree of agglutination by the Behring test and by the Fc test, where the Hyland test gave any degree of agglutination, we found 18 such specimens out of the 189. These 18 specimens broke down into the following which were clearly non-rheumatoid to the best of our capability judging from Waaler-Rose titers, clinical determination, and the total lack of agglutination by both Behring and the Fc particles:

| | | |
|---|---|---|
| | Carcinoma | 3 |
| | VDRL positive | 3 |
| | Cirrhosis | 3 |
| | Pleural affusion | 1 |
| | Alcoholic | 1 |
| | Hyper-gamma | 3 |
| | Miscellaneous | 4 |

In comparing the Hyland results to the Behring results we found that in 34.4%, or in 65 out of the 189 specimens examined, Hyland was always higher in avidity of agglutination than Behring. In comparing the Hyland vs the Fc sensitized particle results we find that Hyland gave a higher degree of avidity of reaction in 40.2% of all the sera tested or 76 out of 189. These data are consistent with the report by MacSween and his colleagues (Jrnl of Clin Path., pg. 368 Vol 27/1974) in which it was shown that the Hyland RF test gave the lowest percentage of correlation with Waaler-Rose negative sera; in other words, it is the least reliable of any of the RF tests studied in giving what we would call false positives with Waaler-Rose negative sera.

These data support the improved specificity in accord with the contention (Ilter and Turner, Clin. exp. Immunol., 1973, 15:93-101) that it is the Fc portion that specifically reacts with the Rheumatoid Factor and therefore this preparation would thus gain enhanced specificity and result in a reduced number of false positives.

The Fc sensitized preparation of cells in this example utilized intact cells but cell wall fragments of the protein A containing cells may also be used in a manner similar to that described herein without deviating from the basic precepts of the invention.

Example 2

The cell preparation of protein A containing *S. aureus* strain G-1 to 8 was prepared as described above in Example 1 up to the 5-7 time washing with PBS 7.3 after which the cells were disrupted utilizing mechanical means such as with an Eperbach micro mill. The addition of 120 micron glass beads facilitates the disruption of the microbial cells. The cell wall particles are separated from other particulate and soluble cytoplasmic content by differential centrifugation and are thoroughly washed with distilled water by repeated centrifugation. The final cell wall material is then lyophilized.

Suspend 10 mg of the washed cell wall suspension as prepared above in 5 ml of phosphate buffered saline, pH 7.4 and the identical amount of Fc fragment preparation as described in Example 1 above is added, after which the same test procedures are performed as described in Example 1; the results were essentially the same, thereby demonstrating the feasibility of sensitizing cell wall fragments of protein A containing microorganisms with the Fc fragments which will then agglutinate in the presence of a Rheumatoid Factor.

Example No. 3

Polysaccharide from cultures of *Cryptococcus neoformens* was prepared as outlined by Bloomfield et al. (Proc. Soc. Exptl. Biol. 2nd Med., 114:-67, 1963).

The Cryptococcus polysaccharide, when suitably injected into rabbits, resulted in antiserum that would react with the Cryptococcus polysaccharide. The serum from rabbits thus immunized was utilized to sensitize both latex particles and protein A-containing Micrococcus cells in order to demonstrate the feasibility of utilizing the latter material as a sensitized agglutinin for detecting the presence of Cryptococcus polysaccharide in clinical specimens.

A stock suspension of 0.81 micron latex particles (Dow, Midland, Michigan) was prepared by mixing 2 ml of a 10% solution of the 0.81 micron latex particles with 28 ml of glycine saline buffer solution at pH 8.2 (GBS). To 0.5 ml of the stock latex suspension prepared as above was added an equal volume of Cryptococcus antiserum prepared from a rabbit (#64179) which serum had been diluted 1:10 using GBS pH 8.2. A similar preparation was made utilizing a 1:50 dilution of the same serum.

A Protein A-containing Micrococcus suspension was prepared as described in Example 1 above and to 0.5 ml of such a cell suspension was added an equal volume of the same serum (rabbit #64179) diluted 1:10; another preparation was made diluted 1:50. These preparations thus constituted four series that were tested by slide agglutination against a serial dilution of a Cryptococcus polysaccharide antigen (87-93F). The following table indicates the reaction in which 4+ would be a very strong slide agglutination test and +/− would be the weakest detectable agglutination test; a negative test is designed by (−).

|  | Antigen | 1:1 | 1:2 | 1:4 | 1:8 | 1:16 | (Control) GBS BSA |
|---|---|---|---|---|---|---|---|
| Dow latex | 1:10 | − | + | +/− | − | − | − |
|  | 1:50 | − | − | − | − | − | − |
| Protein | 1:10 | ++ | ++++ | ++++ | +++ | + | − |
| A-cells | 1:50 | + | + | + | + | + | + | − |

It is clear from the above table that the protein A-containing Micrococcus cells result in a stronger agglutination reaction, other factors of the test being equal. We attribute this enchanded agglutination to the specific adsorption of the IgG globulins from the serum to the protein A-containing particles whereas the latex will adsorb many other proteins from the serum in addition to the immunoglobulins. This is clearly indicated by taking the same serum utilized in this experiment, precipitating the gammaglobulins, and repeating the sensitization with the Dow 0.81 micron latex particles. By utilizing the equivalent amount of gammaglobulin as whole serum it can be shown that a much stronger agglutination test is thereby achieved.

A commercial test for the detection of *Crytococcus neoformens* polysaccharide in clinical material utilizing latex particles has been marketed (Industrial Biological Laboratories, Inc., Rockville, Maryland) and it is clear from the literature for this product that a separate control test has to be performed in order to determine that no false positives result due to the presence of Rheumatoid Factor which may be present in serum negative for Cryptococcus polysaccharide. We have clearly determined that the protein A Micrococcus cells thus sensitized with Cryptococcus antiserum do not react with known Rheumatoid factor-containing sera and thereby thus gain an advantage by insuring the reduction or elimination of potentially false positive reactions as indicated above.

The invention described herein may also be utilized to identify and quantitate immunoglobulins.

EXAMPLE 4

An intact cell suspension as described in Example 1 above, is washed once by centrifugation at 2500 rpm for 15 minutes at 50 C and resuspended in glycine saline buffer pH 8.2. A preparation of sheep anti-human IgA immunoglobulin (alpha-chain specific) was prepared as usually described in the literature.

Add 3.9 ml of the washed cell suspension to 0.1 ml of the sheep anti-IgA serum and the two permitted to react at room temperature for approximately one hour. A series of standardized IgA dilutions are prepared utilizing glycine saline buffer pH 8.2 to result in a twofold dilution starting with 500/ug/ml to 8/ug/ml. One drop of the various dilutions of the standard IgA preparation was placed on a slide and to it was added one drop of the cell preparation sensitized with the sheep Anti-IgA serum and the slide rotated on a rotating shaker at approximately 120 rpm for 5 min. At the end of that time the agglutination were read as follows:

| IgA standards (ug/ml) | 500 | 250 | 125 | 68 | 34 | 17 | 8 | Control (GBS pH 8.2) |
|---|---|---|---|---|---|---|---|---|
| Anti IgA sensitized particles | +++ | +++ | +++ | +++ | + | − | − | − |

It is clear that there's a sharp endpoint at 68/ug/ml beyond which very little, if any, agglutination takes place. This indicates that the sensitzation of the particles has been achieved to detect a minimum of 68 /ug/ml of IgA. The cell preparation thus sensitized was then utilized to test serum from patients where the IgA values had been determined by radial-immunudiffusion and the following results were found.

| Serum No. | Radial Immunudiffusion | Protein A particles |
|---|---|---|
| 71–116A | 274 | 265 |
| 71–116B | <5.0 | <10.0 |
| 71–116C | 185 | 165 |

In order to insure that the sensitized cells were specific for IgA, the serial dilution test was repeated substituting immunoglobulin IgG and IgM in place of IgA with no cross-agglutination being found.

It is clear that the IgA-sensitized Micrococcus particles are specific for IgA since no reaction took place with IgM or IgG. In addition the correlation in the quantitation of the IgA in the patients' serum is within acceptable experimental error consistent with the results found by radial immunodiffusion methods.

We claim:

1. A method of testing for the presence of Rheumatoid Factor in a biological specimen of animal origin, comprising the step of combining the specimen containing the suspected Rheumatoid Factor with a protein A microbial cell suspension sensitized with free Fc fragments of IgG to which Rheumatoid Factor is specific, with resultant agglutination if positive.

2. A method according to claim 1 in which the wall of the microbial cell is fragmented.

3. A method according to claim 1 in which detection is quantitated by combining known serial dilutions of the specimen containing the suspected Rheumatoid Factor with a standard concentration of said suspension so sensitized with free Fc fragments of IgG.

4. A method according to claim 3 in which the wall of the microbial wall is fragmented.

5. A method of testing for the presence of suspected Rheumatoid Factor in serum, comprising the step of combining the serum containing the suspected Rheumatoid Factor with a protein A containing microbial cell suspension sensitized with free Fc fragments of IgG to which Rheumatoid Factor is specific whereby agglutination occurs if the test is positive, and in which the test is quantitated by combining known serial dilutions of the specimen with a standard concentration of said free Fc fragments of IgG sensitized protein A microbial cells.

6. A method according to claim 5 in which the wall of the microbial cell is fragmented.